United States Patent
Chung et al.

(10) Patent No.: US 10,844,394 B2
(45) Date of Patent: Nov. 24, 2020

(54) ACTIVITY OF AHPF PROTEIN OF PSEUDOMONAS AERUGINOSA, AND USE THEREFOR

(71) Applicant: KOREA ATOMIC ENERGY RESEARCH INSTITUTE, Daejeon (KR)

(72) Inventors: Byung Yeoup Chung, Jeollabuk-do (KR); Sudhir Singh, Mumbai (IN); Seung Sik Lee, Jeollabuk-do (KR); Hyoung Woo Bai, Jeollabuk-do (KR); Sung Beom Lee, Jeollabuk-do (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 87 days.

(21) Appl. No.: 16/036,314

(22) Filed: Jul. 16, 2018

(65) Prior Publication Data

US 2018/0346918 A1    Dec. 6, 2018

Related U.S. Application Data

(62) Division of application No. 15/022,296, filed as application No. PCT/KR2013/010564 on Nov. 20, 2013, now abandoned.

(30) Foreign Application Priority Data

Sep. 17, 2013    (KR) .......................... 10-2013-0111916

(51) Int. Cl.
| | | |
|---|---|---|
| *A01H 5/00* | (2018.01) | |
| *C12N 15/00* | (2006.01) | |
| *C12N 15/82* | (2006.01) | |
| *C12N 9/08* | (2006.01) | |

(52) U.S. Cl.
CPC .......... *C12N 15/8271* (2013.01); *A01H 5/00* (2013.01); *C12N 9/0065* (2013.01); *C12N 15/00* (2013.01); *C12Y 108/01009* (2013.01); *C12Y 111/01* (2013.01)

(58) Field of Classification Search
None
See application file for complete search history.

(56) References Cited

U.S. PATENT DOCUMENTS

2011/0265221 A1    10/2011    Abad et al.

FOREIGN PATENT DOCUMENTS

| KR | 10-2012-0042701 A | 5/2012 |
|---|---|---|
| WO | 2009/009142 A2 | 1/2009 |

OTHER PUBLICATIONS

"Alkyl hydroperoxide reductase [Pseudomonas aeruginosa PAO1]" NCBI, GenBank accession No. NP_248830.1, Jul. 22, 2013.
Byung Chull AN et al. A New Antioxidant with Dual Functions as a Peroxidase and Chaperone in Pseudomonas aeruginosa, Molecules and Cells, pp. 145-151, Feb. 28, 2010, vol. 29.
Urs A. Ochsner et al., "Role of the Pseudomonas aeruginosa oxyR-recG Operon in Oxidative Stress Defense and DNA Repair: OxyR-Dependent Regulation of katB-ankB, ahpB, and ahpC-ahpF", Journal of Bacteriology, Aug. 2000, pp. 4533-4544, vol. 182, No. 16.
Prabhakar Salunkhe et al., "Genome-Wide Transcriptional Profiling of the Steady-State Response of Pseudomonas aeruginosa to Hydrogen Peroxide", Journal of Bacteriology, Apr. 2005, p. 2565-2572, vol. 187, No. 8.
Carola A. Neumann et al, "Essential role for the peroxiredoxin Prdx1 in erythrocyte antioxidant defence and tumour suppression", Nature, Jul. 31, 2003, pp. 561-565, vol. 424.
R. B. Horsch et al., "A Simple and General Method for Transferring Genes into Plants", Science, Mar. 8, 1985, pp. 1229-1231, vol. 227.
Toren Finkel, "Oxidant signals and oxidative stress", Current Opinion in Cell Biology, 2003, pp. 247-254, vol. 15.
International Searching Authority, International Search Report of PCT/KR2013/010564 dated Jun. 16, 2014 [PCT/ISA/210].
State Intellectual Property Office of People's Republic of China; Communication dated Sep. 3, 2018 in counterpart application No. 201380079663.0.

*Primary Examiner* — Phuong T Bui
(74) *Attorney, Agent, or Firm* — Sughrue Mion, PLLC

(57)    ABSTRACT

An AhpF protein has thioredoxin reductase, peroxidase, and chaperone activities and is derived from *Pseudomonas aeruginosa*, and a use therefor. By using a novel activity of the AhpF of *Pseudomonas aeruginosa* according to the present invention, it is possible to produce a plant having strong resistance to various environmental stresses such as oxidative stress or heat stress, thereby making it possible to contribute to increasing crop productivity and mass production of useful constituents. In addition, it is possible to prevent desertification and environmental pollution through the development of transformed plants having resistance to high temperatures and drying.

5 Claims, 17 Drawing Sheets

(5 of 17 Drawing Sheet(s) Filed in Color)

Specification includes a Sequence Listing.

[FIG. 1]
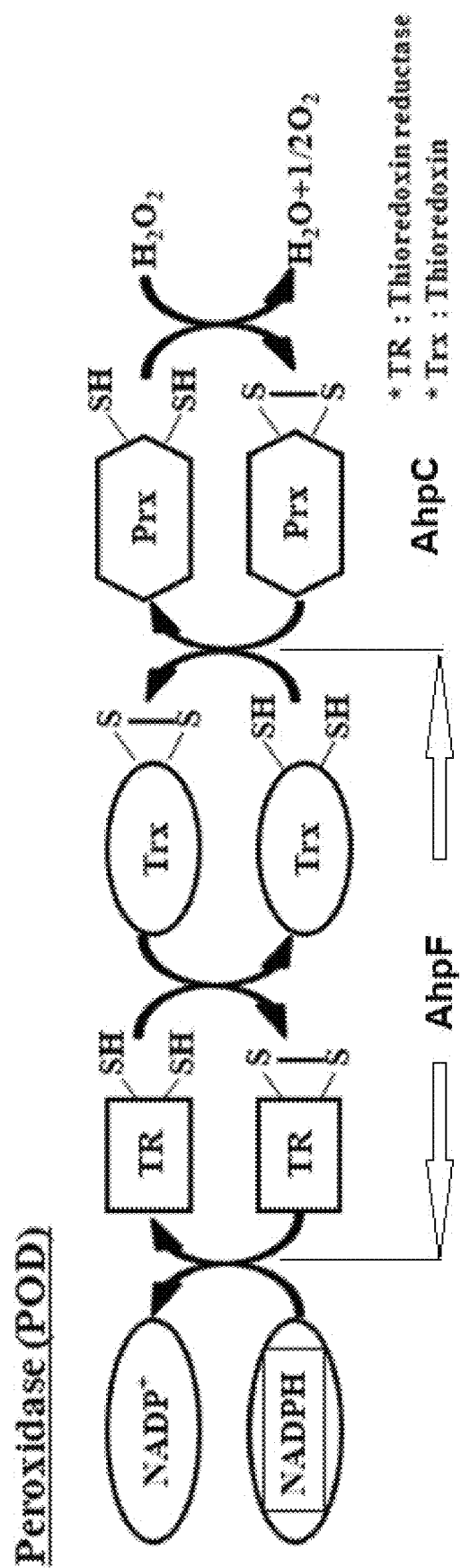

[FIG. 2]
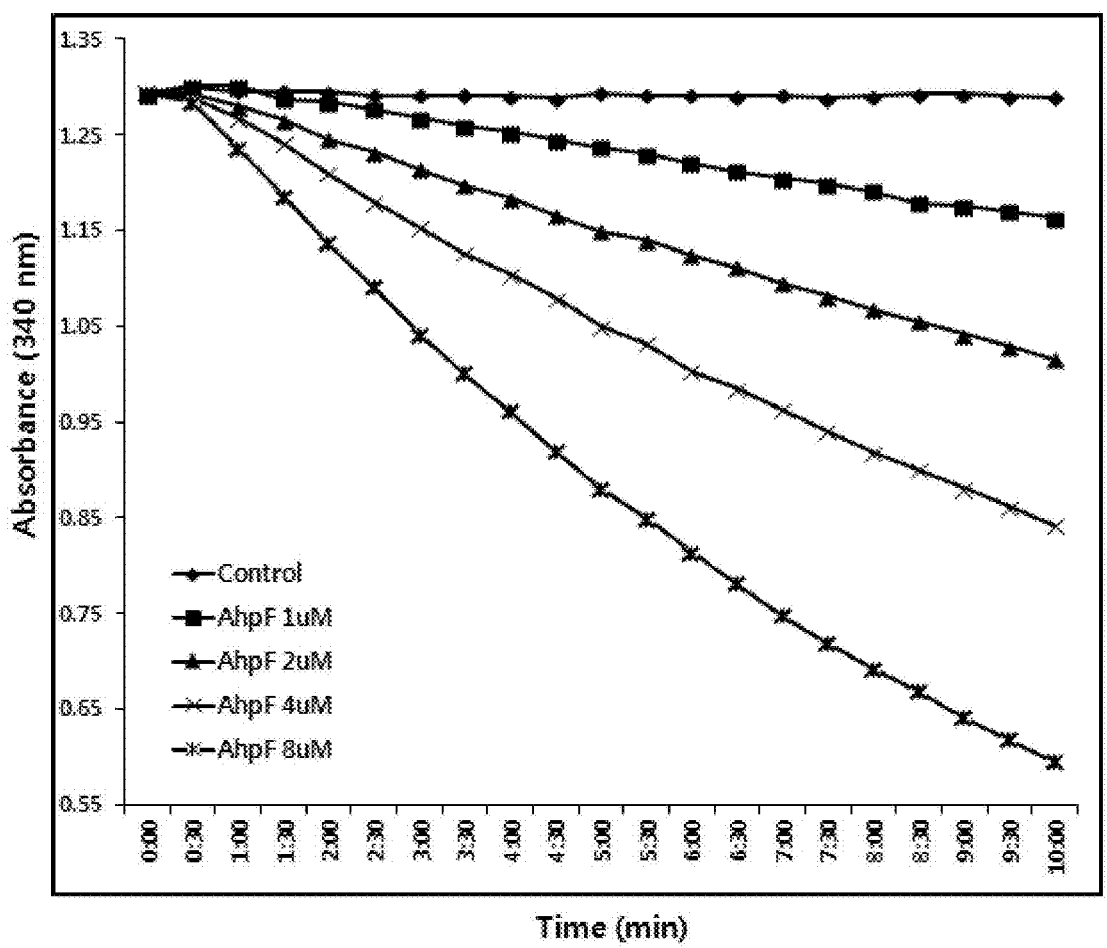

[FIG. 3A]
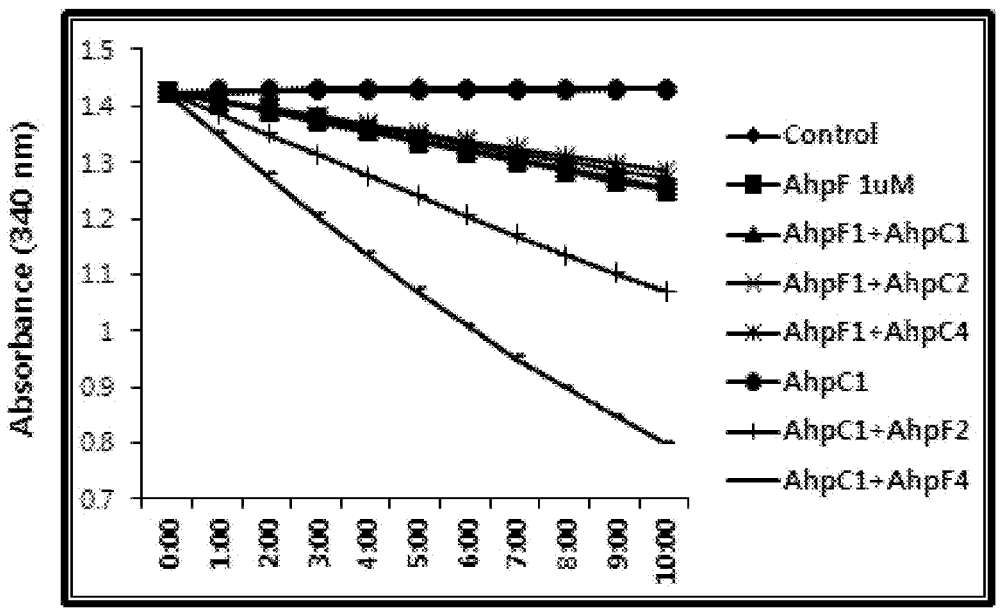
[FIG. 3B]
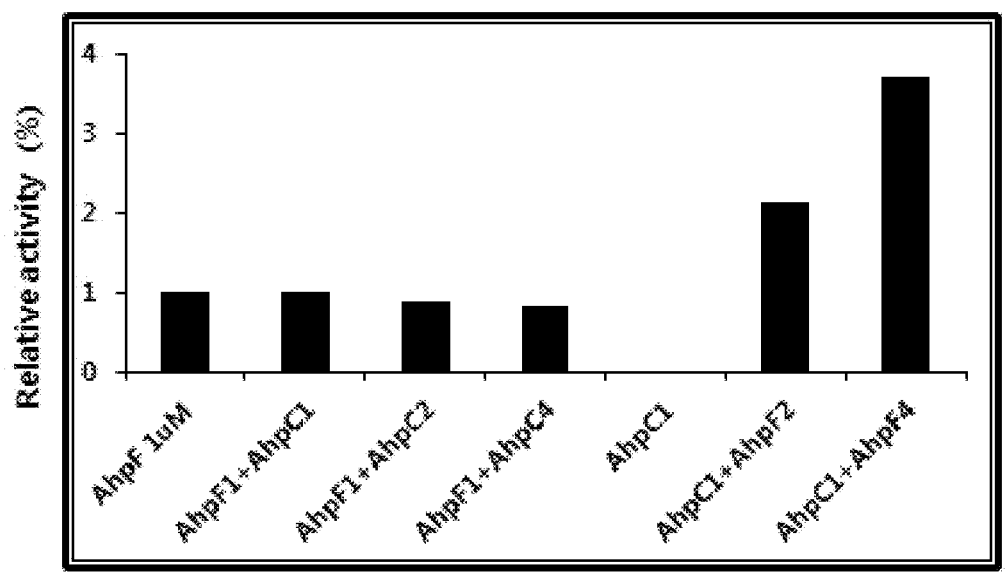

[FIG. 4A]
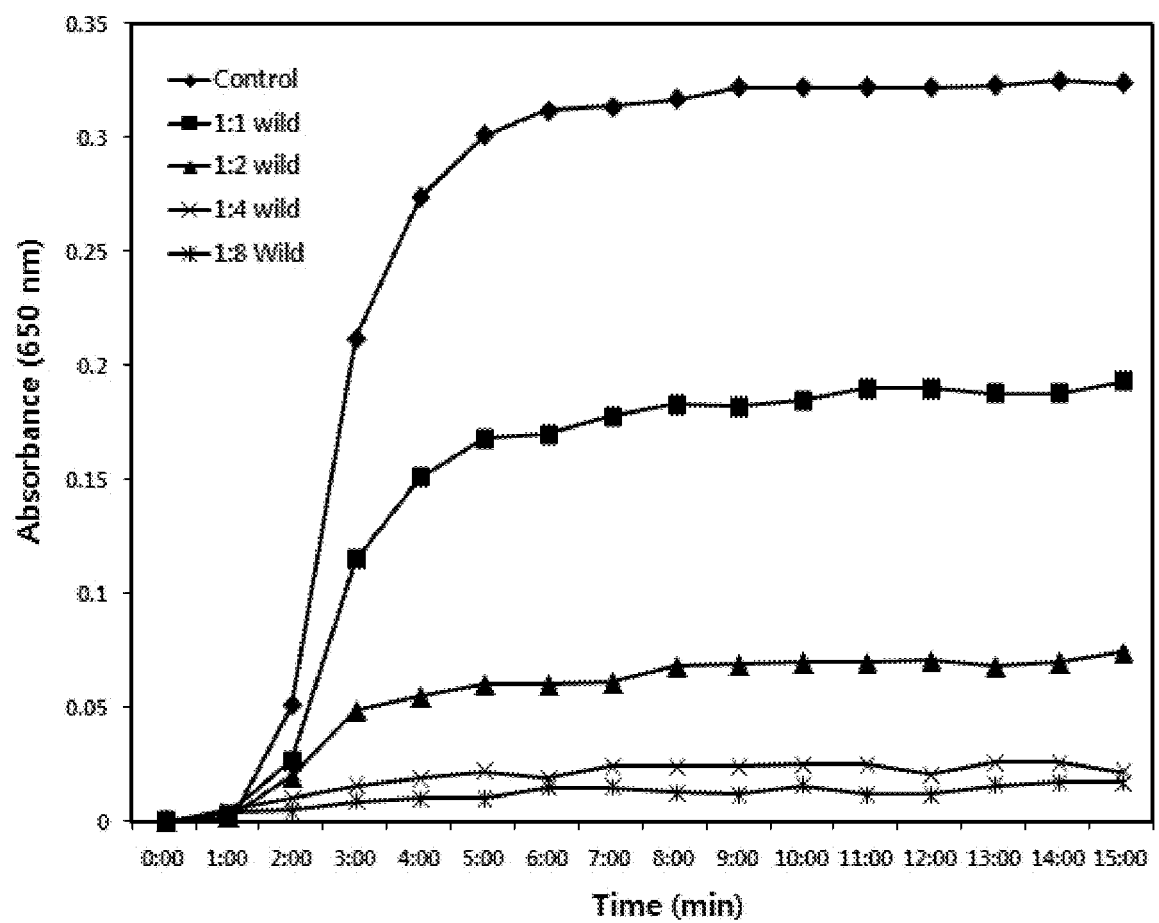

[FIG. 4B]
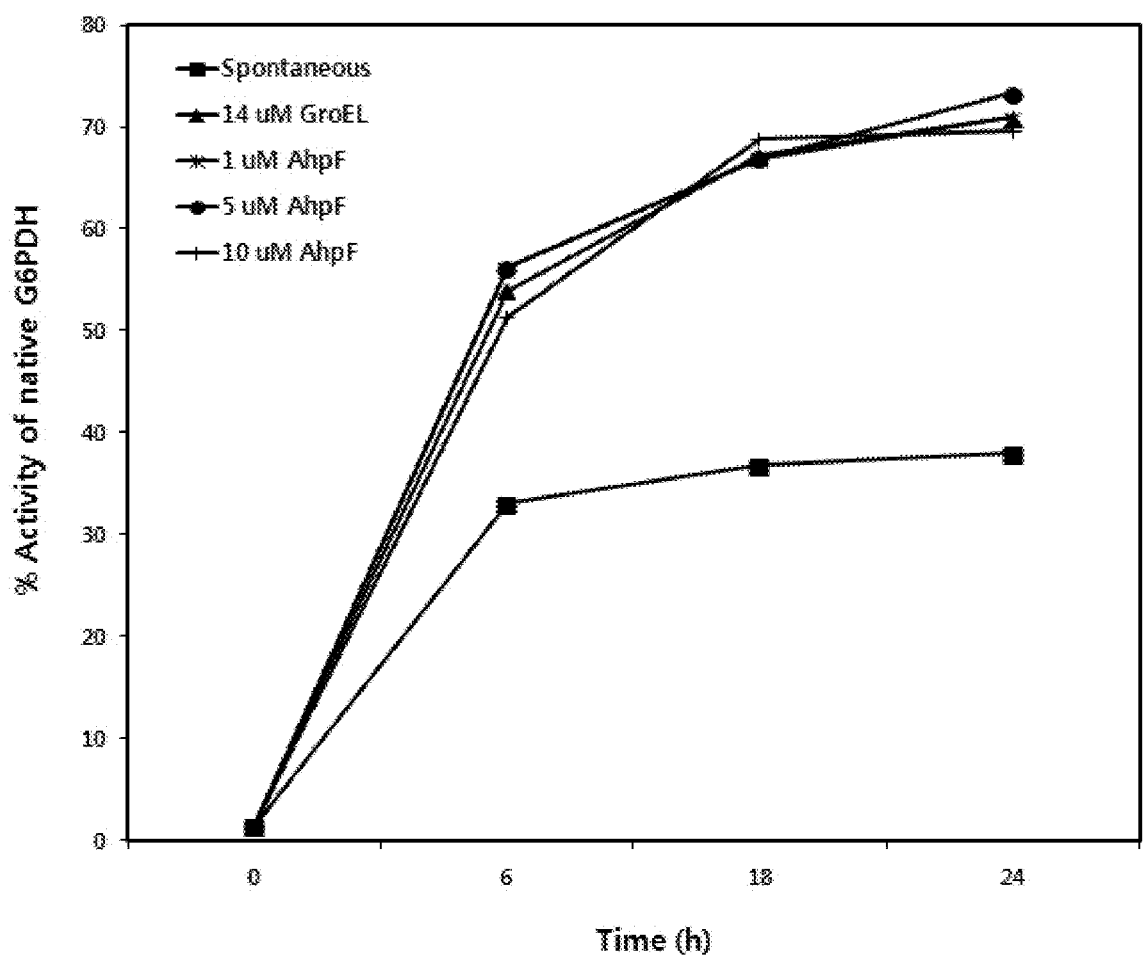

[FIG. 5A]
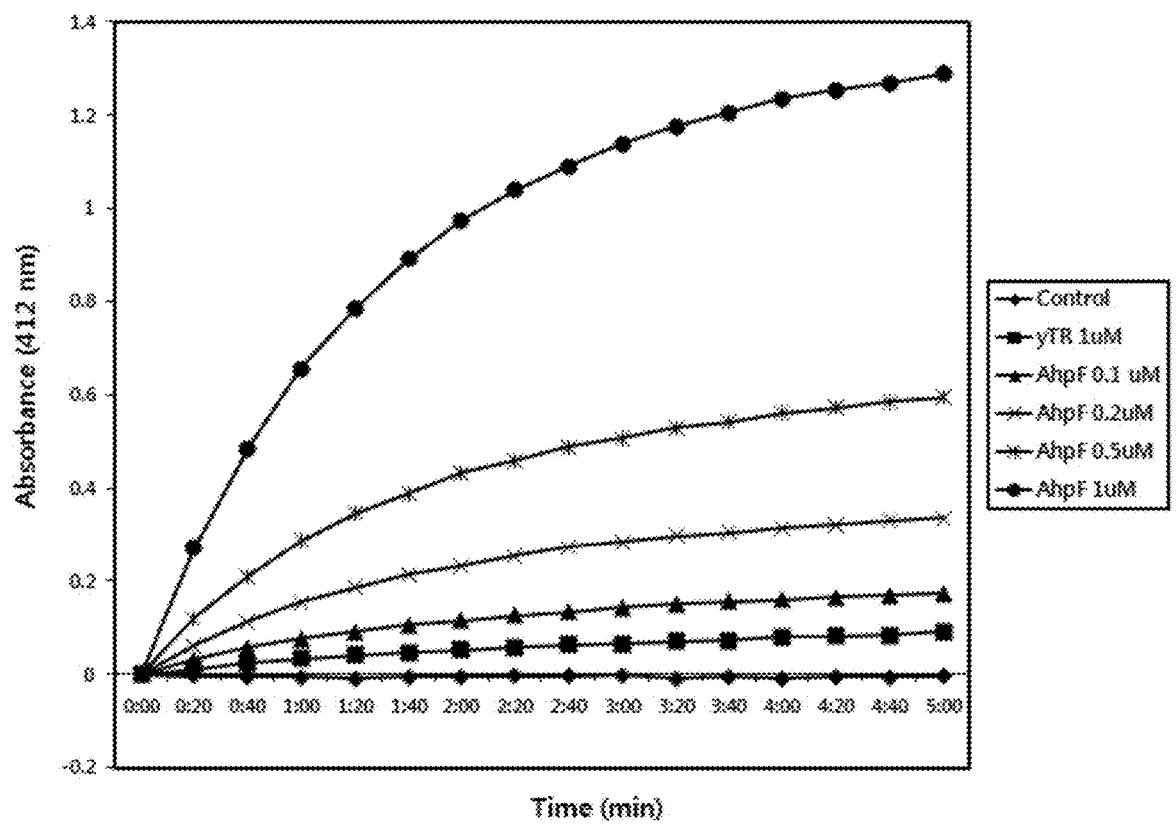

[FIG. 5B]
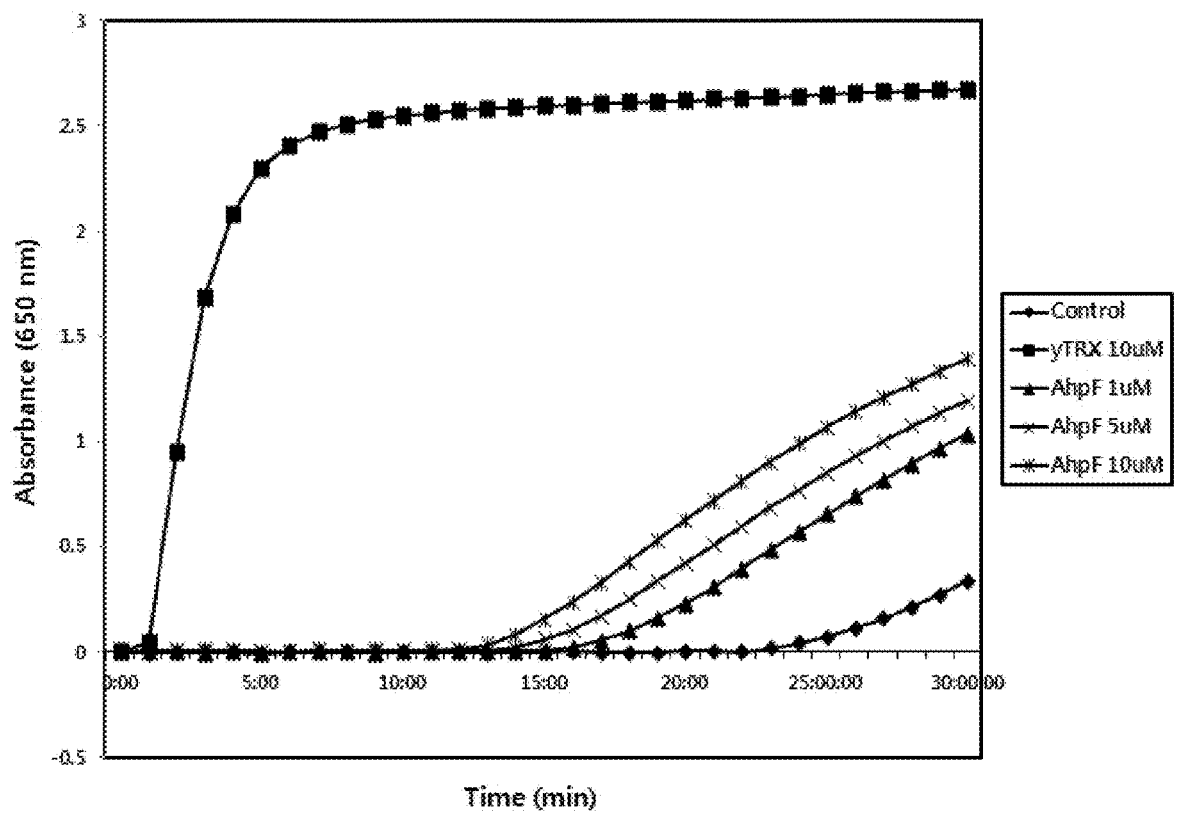

[FIG. 6]
Schematic representation of AhpF
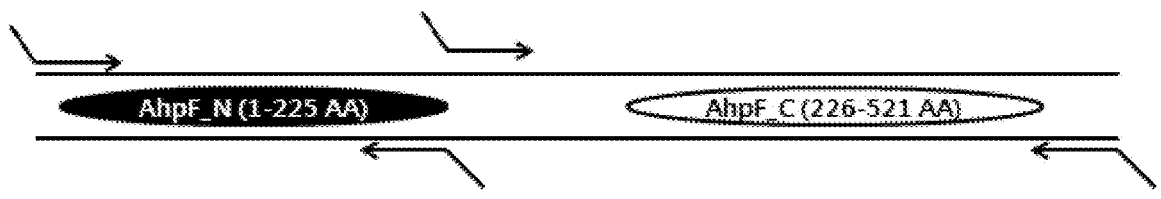
Cloning of C & N-terminal domains of AhpF

[FIG. 7]
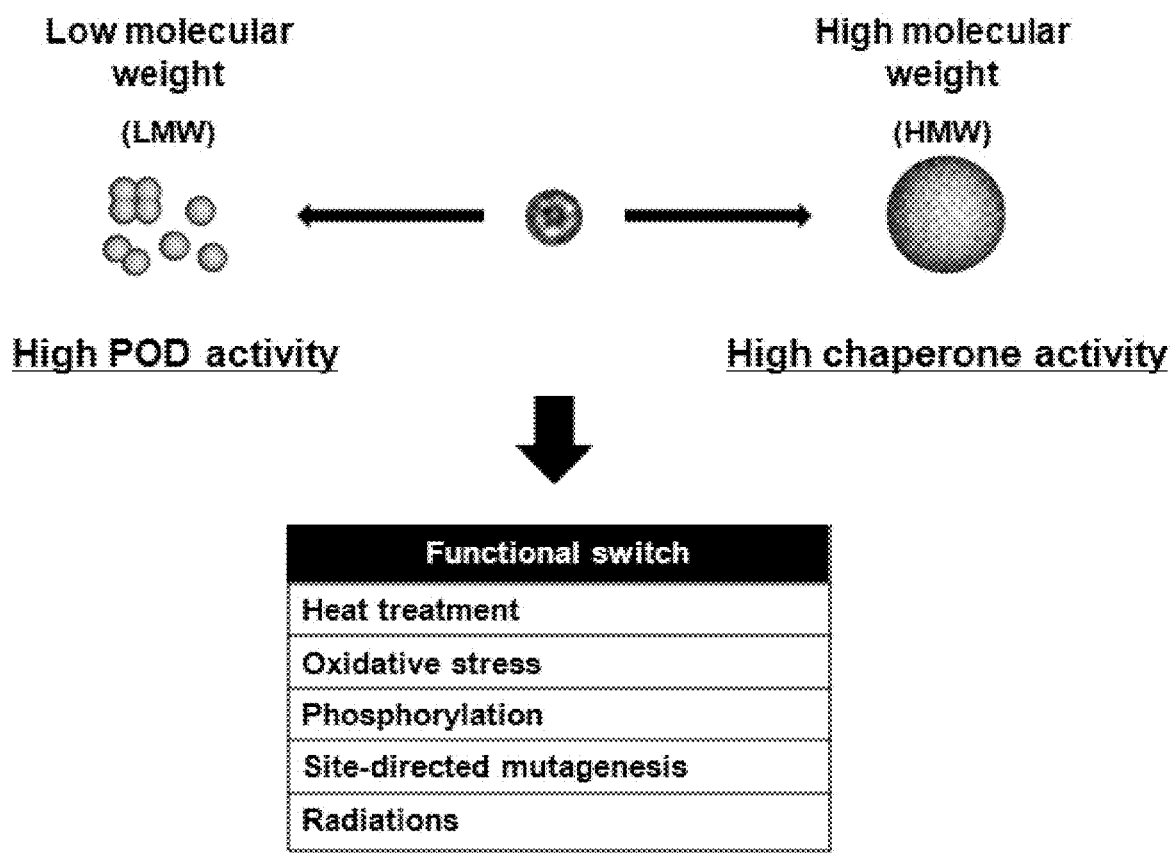

[FIG. 8A]
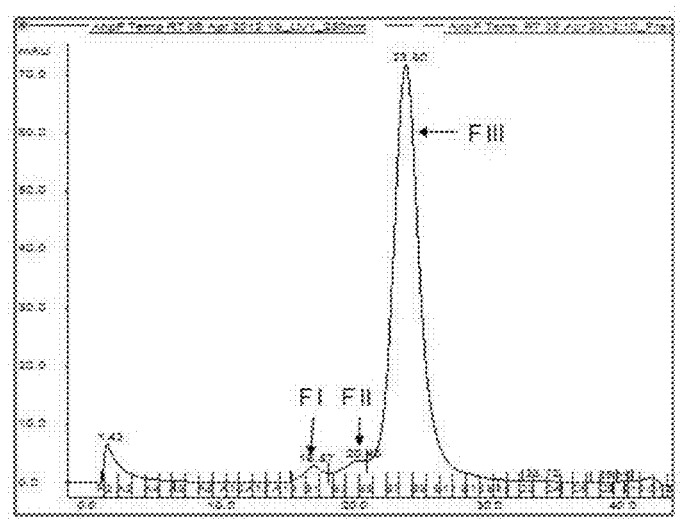
[FIG. 8B]
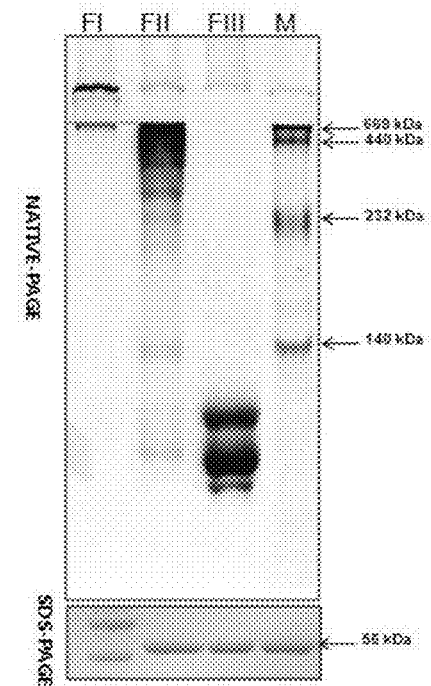

[FIG. 9A]
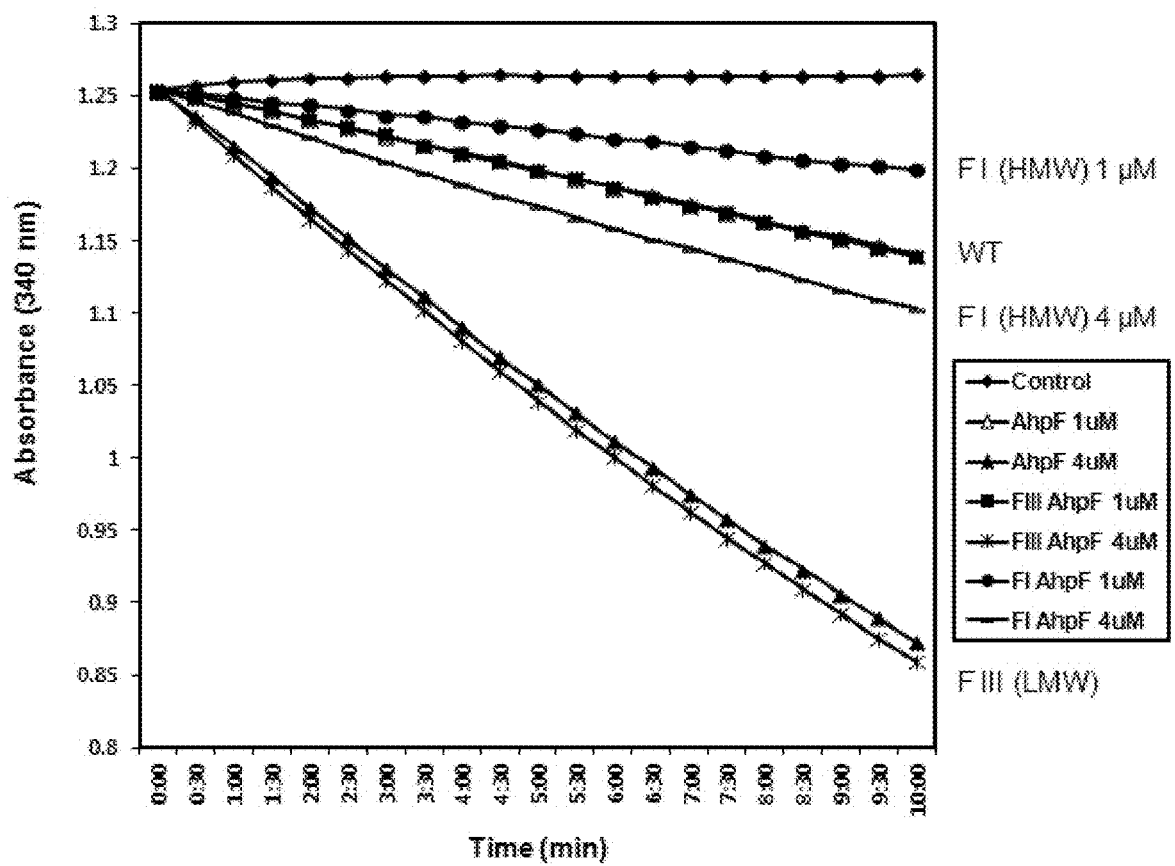

[FIG. 9B]
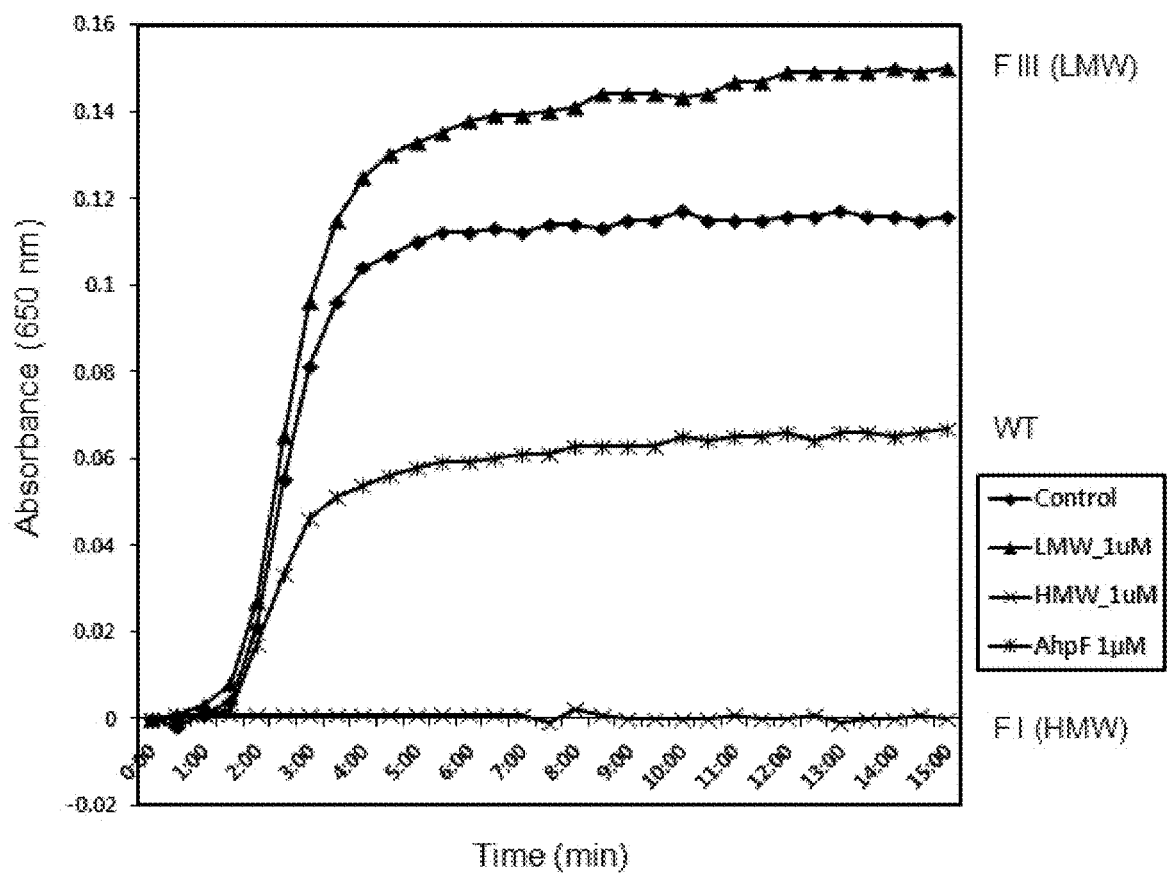

[FIG. 10A]
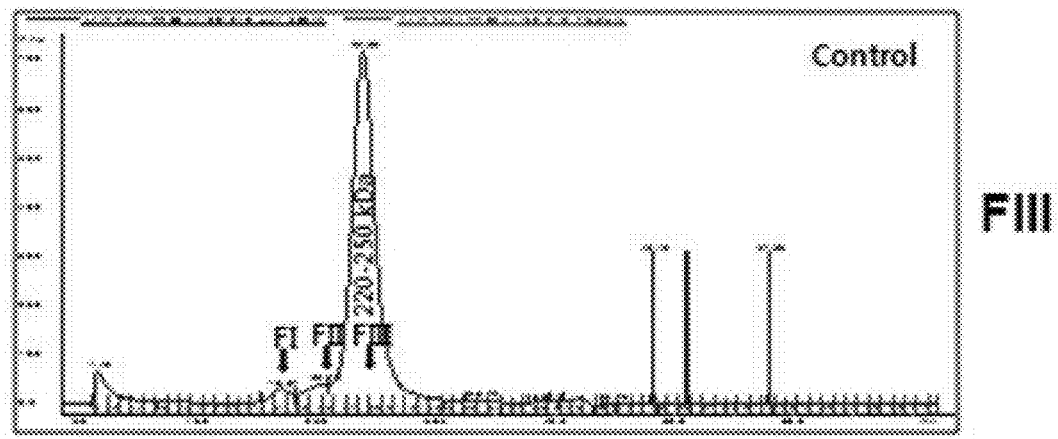
[FIG. 10B]
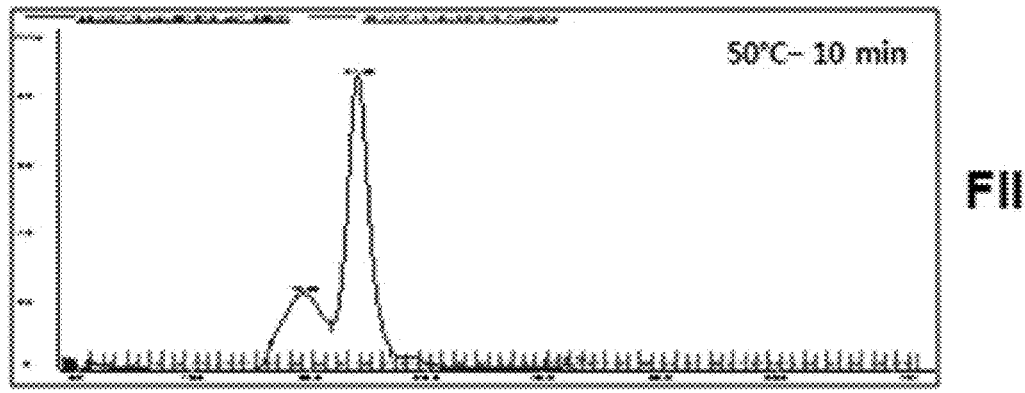
[FIG. 10C]
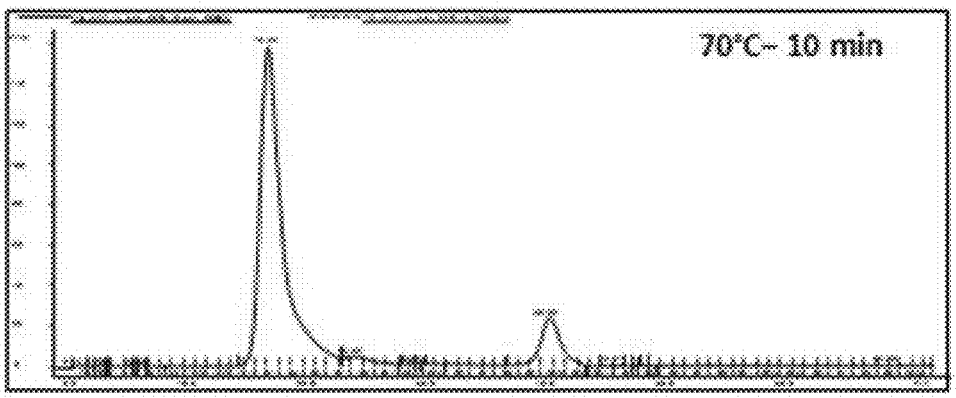

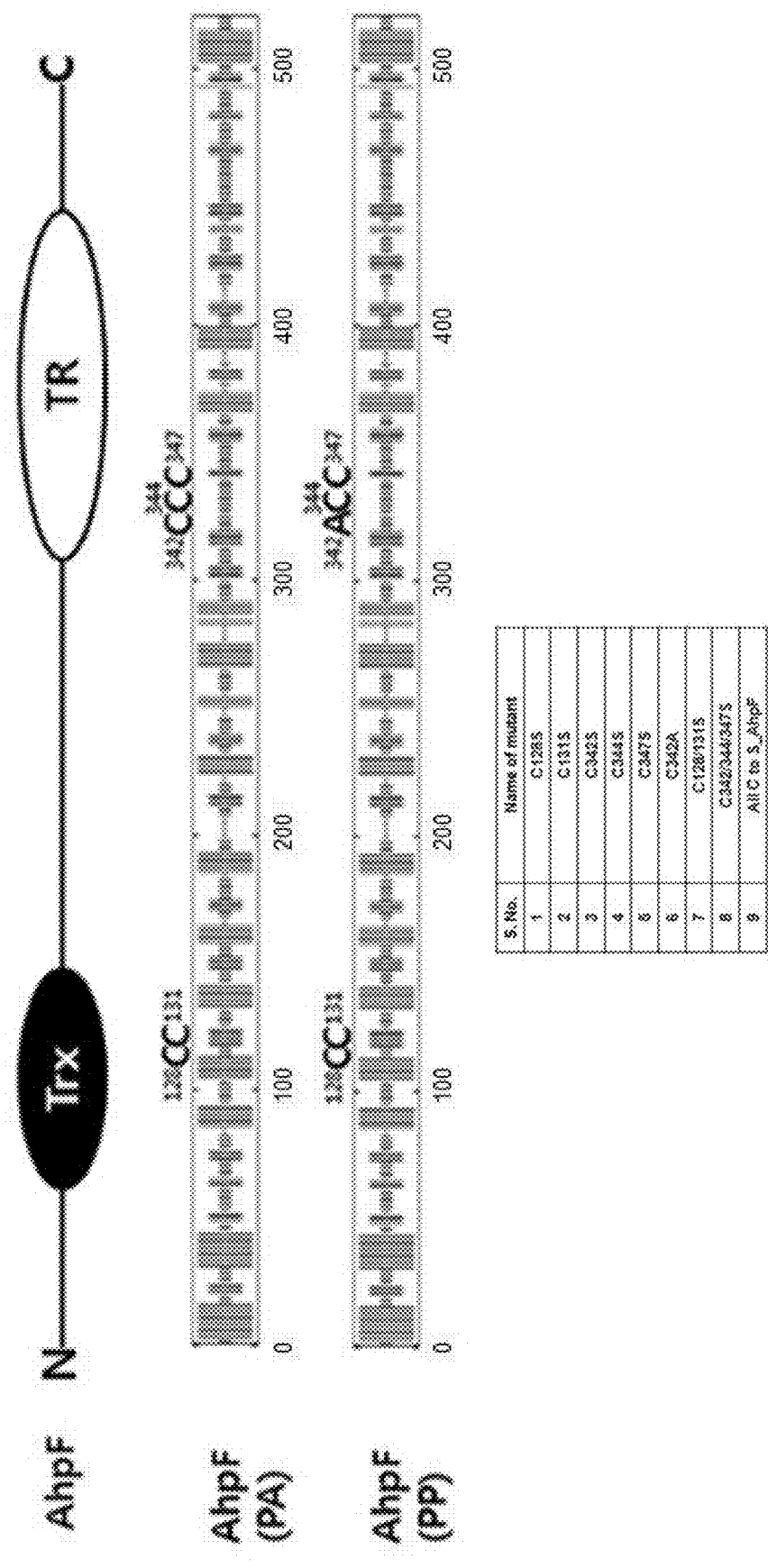
[FIG. 11]

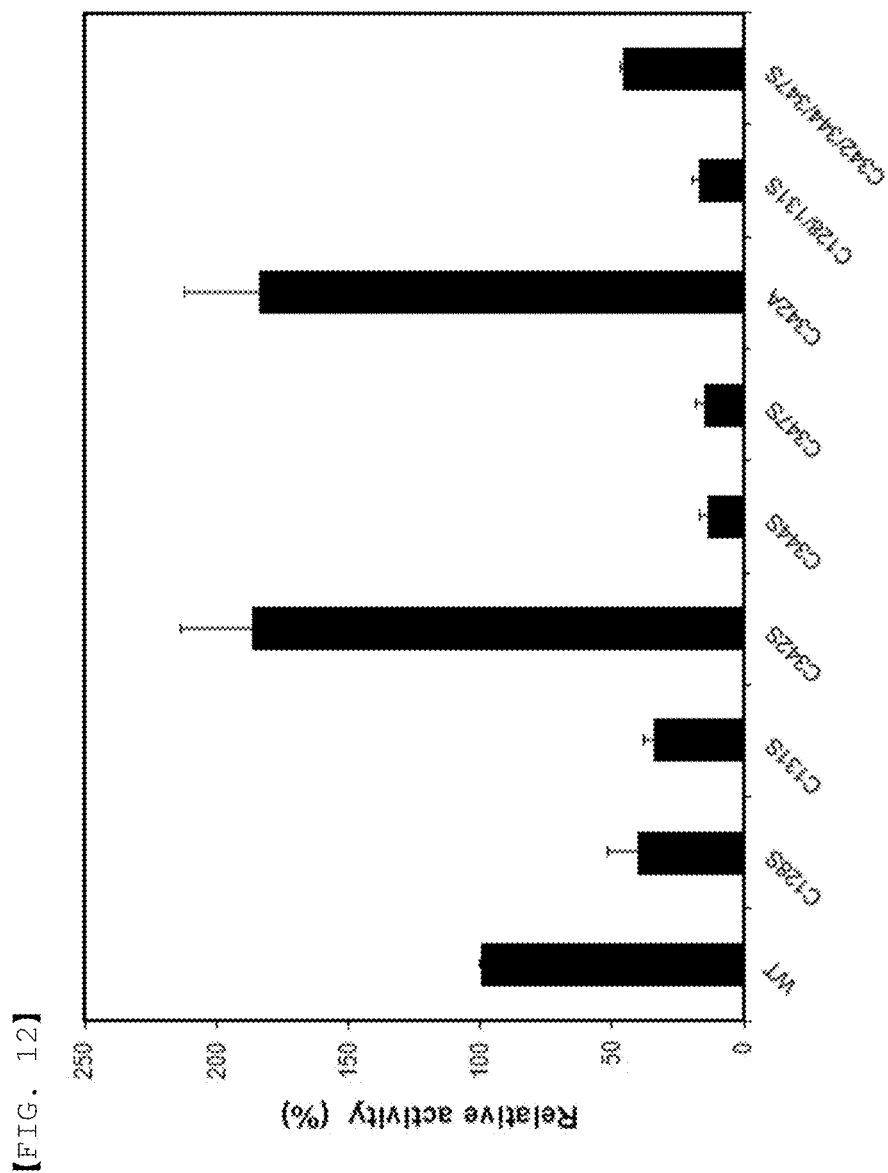
[FIG. 12]

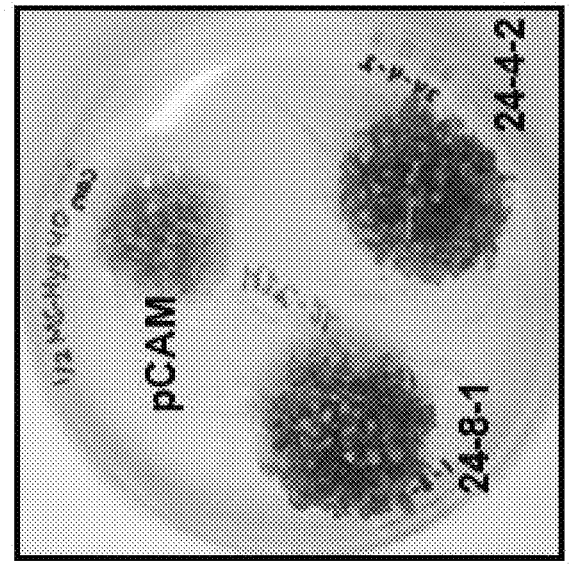
[FIG. 13C]
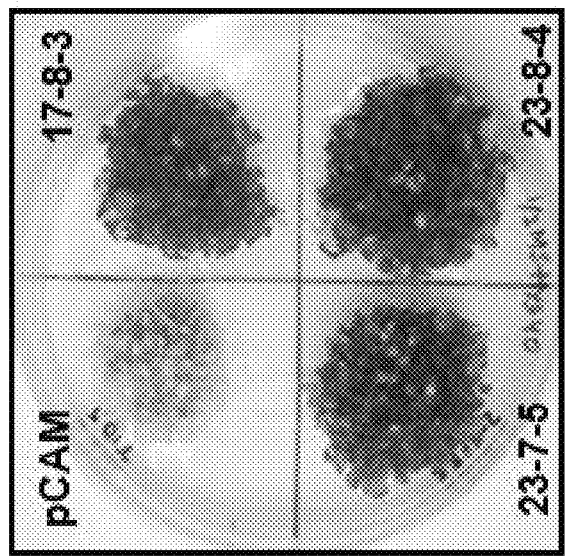
[FIG. 13B]
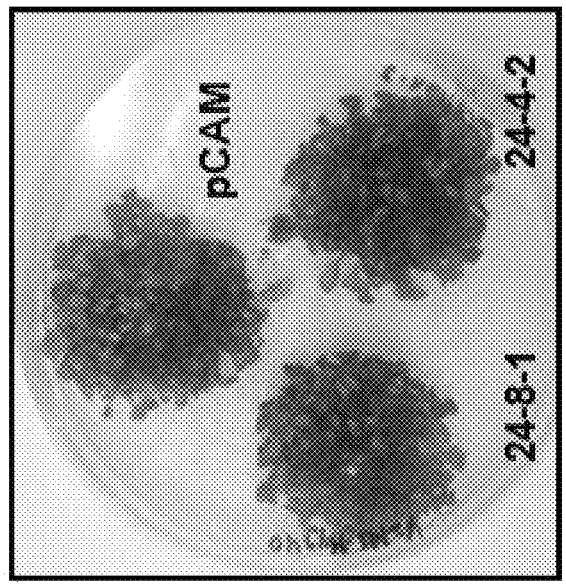
[FIG. 13A]

[FIG. 14A]
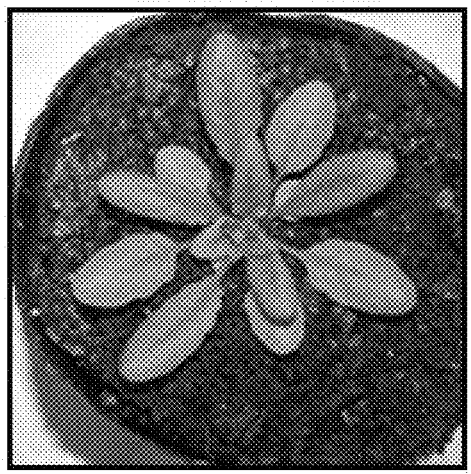
Non-treated
[FIG. 14B]
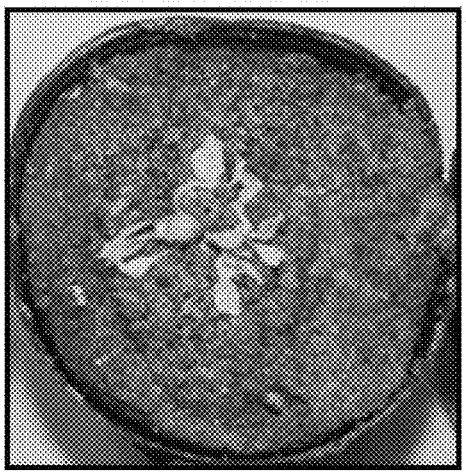
Control
[FIG. 14C]
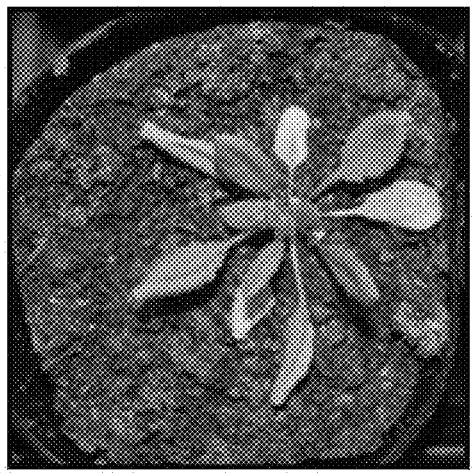
24-8-1
[FIG.14D]
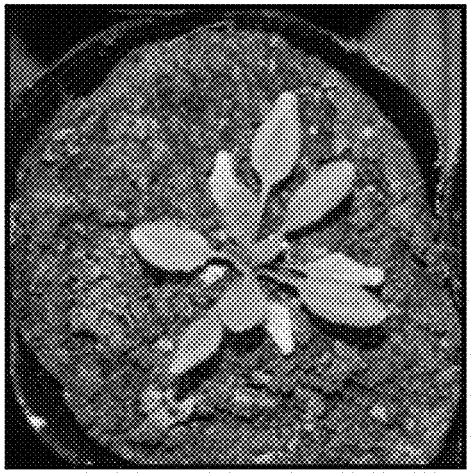
23-8-4
Day 4/37°C

ACTIVITY OF AHPF PROTEIN OF PSEUDOMONAS AERUGINOSA, AND USE THEREFOR

CROSS REFERENCE TO RELATED APPLICATIONS

This application is a Divisional Application of U.S. application Ser. No. 15/022,296, filed Mar. 16, 2016 in the U.S. Patent and Trademark Office, which is a National Stage of International Application No. PCT/KR2013/010564, filed Nov. 20, 2013, now abandoned, claiming priority based on Korean Patent Application No. 10-2013-0111916, filed Sep. 17, 2013, the contents of all of which are incorporated herein by reference in their entirety.

TECHNICAL FIELD

The present invention relates to an alkyl hydroperoxide reductase subunit F (AhpF) protein which has thioredoxin reductase (TR), thioredoxin (Trx), peroxidase (Prx), and chaperone activities and is derived from *Pseudomonas aeruginosa*, and a use therefor. More specifically, according to the present invention, it is newly proven that an AhpF protein has peroxidase and chaperone activities as well as functions of thioredoxin reductase known in the art. Therefore, the present invention relates to a new organism having resistance to environmental stress, produced by introducing a gene encoding the AhpF protein in the organism using the novel activity of the AhpF of *Pseudomonas aeruginosa*, and a method of producing the same.

BACKGROUND ART

Reactive oxygen species (ROS) are generated during the course of aerobic metabolism or when an organism is exposed to a variety of stress conditions (Finkel T., Curr. Opin. Cell Biol. 15: 247-254, 2003). These reactive oxygen species cause serious damage such as oxidative dysfunction or structural changes of biological macromolecules (proteins, lipids, nucleic acids, or the like), or the like, and cause various diseases (Neumann et al., Nature, 424: 561-565, 2003). All aerobic organisms have diverse forms of molecular chaperones such as heat shock protein in addition to various anti-oxidant proteins in order to protect themselves from oxidative stress or denaturation of proteins mediated by the reactive oxygen species and protein aggregation induced from the denaturation as described above. Among them, *Pseudomonas aeruginosa*, which is a representative Gram-negative bacterium and an opportunistic human pathogen found through nosocomial infections, has strong defense mechanism against the reactive oxygen species. As the specific defense mechanism, *Pseudomonas aeruginosa* has two superoxide dismutases (SOD), three catalases (CAT), and four Ahp reductases.

Meanwhile, it is reported that an Ahp reductase system acts as a defense system against oxidative stress, or the like, in various microbes as well as *Pseudomonas aeruginosa*. The Ahp reductase system may serve to remove the reactive oxygen species harmful in organism by catalyzing NAD(P)H dependent reduction of organic peroxide or hydroperoxide. The Ahp reduction system is generally composed of AhpF-AhpC, and it was reported that among the composition, the alkyl hydroperoxide reductase subunit F (AhpF) is composed of polynucleotide of 1566 bp and 521 amino acids, and has a molecular weight of about 56 kDa.

It was known that AhpC and AhpF in the Ahp reductase system reported in *E. coli, Salmonella typhimurium*, or the like, according to the related art play separate roles, respectively, as illustrated in FIG. 1.

That is, general AhpF in *E. coli, Salmonella typhimurium*, or the like, serves as reductase receiving electrons from NAD(P)H to transfer the electrons to AhpC, and AhpC serves as peroxidase removing hydrogen peroxide ($H_2O_2$). Therefore, it was known that both AhpF and AhpC are required in order to effectively remove the reactive oxygen species.

However, the present inventors initially proved that AhpF of *Pseudomonas aeruginosa* has a peroxidase activity, which is known as an activity of AhpC, a chaperone activity, and the like, as well as a reductase activity, which is known as a general function of AhpF of microbes according to the related art, such that a single AhpF protein may perform various functions. In addition, the present inventors confirmed that an activity of the AhpF protein as described above is structure-dependent, thereby completing the present invention.

DISCLOSURE

Technical Problem

An object of the present invention is to provide an AhpF protein having thioredoxin reductase, peroxidase, and chaperone activities.

Another object of the present invention is to provide a mutant of an AhpF protein of *Pseudomonas aeruginosa* of which a thioredoxin reductase is increased, a high molecular weight complex of AhpF of which a chaperone activity is increased, and a low molecular weight complex of AhpF of which a peroxidase activity is increased.

Another object of the present invention is to provide a composition for improving resistance of organisms to environmental stress, containing a polynucleotide encoding an AhpF protein of *Pseudomonas aeruginosa*, and a plant having resistance to environmental stress, transformed by the polynucleotide.

Technical Solution

In one general aspect, there is provided an AhpF protein of *Pseudomonas aeruginosa* which has all thioredoxin reductase (TR), thioredoxin (Trx), peroxidase (Prx), and chaperone activities.

The AhpF protein of *Pseudomonas aeruginosa* may preferably have an amino acid sequence of SEQ ID No: 1, but is not limited thereto.

In another general aspect, there is provided a mutant of an AhpF protein of *Pseudomonas aeruginosa* of which cysteine at the position 342 of an amino acid sequence of SEQ ID No: 1 is substituted with serine or alanine.

In another general aspect, there are provided high and low molecular weight complexes of the AhpF protein as described above. The high molecular weight complex of the AhpF protein may be characterized in that a chaperone activity is increased, and a molecular weight thereof is at least 500 to 2000 kDa. The low molecular weight complex of the AhpF protein may be characterized in that a peroxidase activity is increased, and a molecular weight thereof is at least 100 to 250 kDa.

In another general aspect, there is provided a composition for improving resistance of organisms to environmental stress, containing a vector into which a polynucleotide encoding an AhpF protein of *Pseudomonas aeruginosa* is introduced.

In another general aspect, there is provided a bacterium in the *Agrobacterium* genus transformed by a recombinant vector expressing the AhpF protein of *Pseudomonas aeruginosa* as described above, and a plant transformed so as to over-express the AhpF protein to thereby have resistance to environmental stress.

In another general aspect, there is provided a method of producing a plant having resistance to environmental stress, characterized in that the plant is transformed using a recombinant vector containing a polynucleotide encoding the AhpF protein.

Hereinafter, the present invention will be described in detail. Unless otherwise defined, terms, technologies, and the like, used in the present specification have the general meaning used in the art to which the present invention pertains. In addition, a repetitive description will be omitted.

An aspect of the present invention relates to the AhpF protein of *Pseudomonas aeruginosa* which has all thioredoxin reductase (TR), thioredoxin (Trx), peroxidase (Prx), and chaperone activities. The AhpF protein of *Pseudomonas aeruginosa* may preferably have an amino acid sequence of SEQ ID No: 1, but is not limited thereto. Even though amino acids of the AhpF protein are partially modified or deleted, all AhpF proteins of *Pseudomonas aeruginosa* having all of the thioredoxin reductase (TR), peroxidase (Prx), and chaperone activities and a homology of 90% or more, which may be easily derived by those skilled in the art, are included in the scope of the present invention.

According to the related art, it was known that the AhpF protein of *Pseudomonas aeruginosa* has only thioredoxin reductase (TR) and thioredoxin (Trx) activities, but the present inventors initially proved that the AhpF protein of *Pseudomonas aeruginosa* also has peroxidase and chaperone activities of AhpC, which were known as functions distinguished from each other, in addition to the TR and Trx activities (see FIG. 1). In Examples of the present invention, it was confirmed that the AhpF protein of *Pseudomonas aeruginosa* has all functions of thioredoxin reductase, thioredoxin, peroxidase, and holdase and foldase of chaperone (see FIGS. 2 to 5).

The peroxidase activity means a process of allowing NADPH to transfer an electron (H$^+$) to thioredoxin reductase (TR) while being converted into NADP$^+$, allowing TR to be oxidized again while transferring the electron to thioredoxin (Trx), allowing Trx reduced by receiving the electron from TR to be oxidized while transferring the electron to Prx, and allowing reduced Prx to decompose H$_2$O$_2$ into O$_2$ and H$_2$O.

In addition, chaperone is a protein participating in folding of proteins. For example, when a protein is exposed to stress such as heat shock, a properly folded three-dimensional structure of the protein may be unfolded, such that the protein may not normally perform its roles. Here, proteins of a group referred to as chaperone mean proteins serving to recognize and bind to the unfolded protein as described above to prevent denaturation of the protein or serving to provide a good environment in which the protein may be proper folding. A molecular chaperone activity may be divided into a holdase and a foldase activity. When the protein is exposed to stresses (oxidative stress, heat stress), a folded three-dimensional structure is partially unfolded by denaturation, hydrophobic regions are exposed, and as a result, in a case in which this process is aggregated, the denatured proteins are irregularly aggregated with each other to thereby be changed into aggregates and removed by protease. At this time, holdase, for example, serves to prevent chaperone proteins (sHSPs, DnaJ) from binding to hydrophobic regions of proteins partially unfolded by stress to form aggregates and serves to create an environment in which the partially unfolded protein may return to an original structure in this case. When a novel protein is synthesized by a ribosome protein using mRNA as a template, the protein is folded into an originally set three-dimensional structure. At this time, foldase, for example, serves to create and assist an environment in which the chaperone proteins (GroEL/ES, DnaK/J/E) bind to newly extended amino acid chains or denatured protein to thereby be folded into an accurate three-dimensional structure.

Another aspect of the present invention relates to the high and low molecular weight complexes of the AhpF protein of *Pseudomonas aeruginosa*. The AhpF protein of *Pseudomonas aeruginosa* according to the present invention has a structure of a homo-oligomeric complex having various molecular weights, and in a high molecular weight (HMW) complex, the function of the chaperone is prominently exhibited. Particularly, it was confirmed that the chaperone activity was increased. In Examples of the present invention, it was confirmed that when exposed to heat shock, a structure of the AhpF protein was changed to the high molecular weight complex, and among the functions of chaperones, a holdase activity was increased (See FIGS. 8 and 10). Further, in the case of AhpF according to the present invention, the peroxidase activity was prominent in the low molecular weight (LMW) complex. A molecular weight of the high molecular weight complex of the AhpF protein may be at least 500 to 2000 kDa. That is, it was found that the high molecular weight complex has a structure in which a monomer of the AhpF protein was larger than at least a tetramer. The molecular weight of the high molecular weight complex of the AhpF protein may be preferably at least 500 to 2000 kDa.

In addition, a molecular weight of the low molecular weight complex of the AhpF protein may be at least 100 to 250 kDa (dimer to tetramer). In the Examples for analyzing a structure of the AhpF protein according to the present invention, when heat stress was not applied, the most general structure was a tetramer.

Another aspect of the present invention relates to a mutant of the AhpF protein of *Pseudomonas aeruginosa*. In the mutant of the AhpF protein, cysteine, which is an amino acid at the position 342 in the amino acid sequence of SEQ ID No: 1, may be substituted with serine or alanine, but is not limited thereto. The AhpF protein according to the present invention includes a Trx domain at an amino terminal, and a TR domain at a carboxyl terminal (see FIG. 11). Cysteine at the position 342 is included in the TR domain. In the Examples of the present invention, the thioredoxin reductase activity of the mutant of the AhpF protein was about 2 times higher than that of wild-type AhpF protein. Further, in the case of substituting cysteine at the position 344 or 347, which is another cysteine in the TR domain, with serine, rather, there was almost no TR activity.

A new fact that the AhpF protein derived from *Pseudomonas aeruginosa* may perform functions of peroxidase and chaperone as well as function of the reductase known in the art was found. Therefore, the present invention relates to application of characteristics of the AhpF protein of *Pseudomonas aeruginosa*.

Another aspect of the present invention associated with the applications of the characteristics of the AhpF protein relates to a composition for improving resistance of organisms to environmental stress, containing a vector into which a polynucleotide encoding an AhpF protein of *Pseudomonas aeruginosa* is introduced. In the composition, as the vector for introducing the polynucleotide encoding the AhpF protein, a vector generally known in the art to which the present invention pertains may be used. Preferably, a pCAMBIA vector may be used. Further, the vector may include a promoter operationally linked to the introduced polynucleotide of the AhpF, and a selection marker gene. The promoter operationally linked to the polynucleotide of the AhpF may express the AhpF or increase expression of the AhpF. The polynucleotide encoding an AhpF protein of *Pseudomonas aeruginosa*, introduced into the vector may preferably encode an AhpF protein of SEQ ID No: 1 or an AhpF protein of *Pseudomonas aeruginosa* in which cysteine at the position 342 in SEQ ID No:1 is mutated to serine or alanine, but is not limited thereto. Since the AhpF protein of SEQ ID No: 1 according to the present invention has all of the thioredoxin reductase, thioredoxin, peroxidase, and chaperone activities, the AhpF protein of SEQ ID No: 1 may allow the organism to have excellent resistance to environmental stress. Further, since the thioredoxin reductase activity of the AhpF protein of *Pseudomonas aeruginosa* in which cysteine at the position 342 in SEQ ID No:1 is mutated to serine or alanine is increased by 2 times or more as compared to the wild-type AhpF protein, thereby making it possible to allow organisms to have resistance to environmental stress. In addition, since in a high molecular weight complex of the AhpF protein of *Pseudomonas aeruginosa* according to the present invention, the chaperone activity is prominent, in the case of using these characteristics, it is possible to increase resistance of organisms to diverse forms of environmental stresses (heat shock, oxidative stress, pathogen, and the like).

Further, the present invention relates to a bacterium in the *Agrobacterium* genus transformed by a recombinant vector expressing the AhpF protein of *Pseudomonas aeruginosa* as described above. The bacterium in the *Agrobacterium* genus may be transformed so as to express the AhpF protein by introducing the recombinant vector into which an AhpF gene is introduced into the bacterium in the *Agrobacterium* genus. The AhpF protein of *Pseudomonas aeruginosa* may be preferably an AhpF protein of SEQ ID No: 1, or an AhpF protein of *Pseudomonas aeruginosa* in which cysteine at the position 342 in SEQ ID No:1 is mutated to serine or alanine. The bacterium in the *Agrobacterium* genus may be preferably *Agrobacterium tumerfaciens*, but is not limited thereto. In addition, all bacteria capable of transforming a plant as well as the bacterium in the *Agrobacterium* genus may also be included in the present invention.

In addition, another aspect of the present invention relates to a plant transformed so as to over-express the AhpF protein of *Pseudomonas aeruginosa* to thereby have resistance to environmental stress. The plant may be a dicotyledonous plant or monocotyledonous plant. Preferably, the plant may be *Arabidopsis thaliana, Brassica rapa*, or *Oryza sativa*. However, the plant is not limited thereto, but all of the plants capable of being transformed so as to over-express the AhpF protein according to the present invention may be included in the present invention. The AhpF protein of *Pseudomonas aeruginosa* over-expressed in the plant may be preferably an AhpF protein of SEQ ID No: 1, or an AhpF protein of *Pseudomonas aeruginosa* in which cysteine at the position 342 in SEQ ID No:1 is mutated to serine or alanine.

In addition, the plant capable of being transformed may be preferably produced by introducing the bacterium in the *Agrobacterium* genus expressing the AhpF protein according to the present invention into a plant cell line, but is not limited thereto.

Further, the present invention relates to a method of producing a plant having resistance to environmental stress, characterized in that the plant is transformed using a recombinant vector containing a polynucleotide encoding the AhpF protein. The polynucleotide encoding an AhpF protein of *Pseudomonas aeruginosa*, contained in the recombinant vector may preferably encode the AhpF protein of SEQ ID No: 1 or the mutated AhpF protein of *Pseudomonas aeruginosa* in which cysteine at the position 342 in SEQ ID No:1 according to the present invention is mutated to serine or alanine, but is not limited thereto.

For transformation of the plant, an *Agrobacterium*-mediated transformation method, and a method disclosed in a document (written by Horsch et al., Science 227:1229-1231, 1985) may be used. In the method of producing a plant having resistance to environmental stress, the recombinant vector may be preferably introduced into *Agrobacterium tumefaciens* to transform the plant, but is not limited thereto. That is, all preferable bacteria capable of transforming a plant such as *Agrobacterium rhizogenes*, and the like, in addition to *Agrobacterium tumefaciens* may be used.

Advantageous Effects

According to the present invention, a plant having strong resistance to various environmental stresses such as oxidative stress, heat stress, or the like, may be produced using a new activity of AhpF of *Pseudomonas aeruginosa*, which may contribute to increasing crop productivity and mass production of useful constituents. In addition, the present invention may be usefully utilized in developing a plant resistant even with severe changes in the environment such as abnormal climate changes due to global warming, drought, drying, and the like, such that desertification and environmental pollution may be prevented through the development of plants transformed so as to have resistance to a high temperatures and drying. Further, it is possible to assist in solving human food shortages by introducing a gene encoding the AhpF protein into a useful crop.

DESCRIPTION OF DRAWINGS

The patent or application file contains at least one drawing executed in color. Copies of this patent or patent application publication with color drawing(s) will be provided by the Office upon request and payment of the necessary fee.

FIG. 1 is a mimetic view comparing activities of AhpF (PaAhpF) of *Pseudomonas aeruginosa* according to the present invention with activities of AhpF and AhpC of *E. coli* or *Salmonella typhimurium* known in the art.

FIG. 2 illustrates a peroxidase activity depending on a concentration of the AhpF according to the present invention.

FIG. 3A and FIG. 3B illustrate an influence of peroxidase activities of AhpF and AhpC of *Pseudomonas aeruginosa*.

FIGS. 4A and 4B illustrate a holdase (FIG. 4A) and a foldase chaperone activity (FIG. 4B) depending on a concentration of AhpF according to the present invention.

FIGS. 5A and 5B illustrate a thioredoxin reductase (TR) activity (FIG. 5A) and thioredoxin (Trx) activity (FIG. 5B) of AhpF according to the present invention.

FIG. 6 is a mimetic view illustrating a structure of an AhpF protein according to the present invention, and illustrating a cloning method for producing mutants of amino acids included in respective terminals according to the present invention.

FIG. 7 is a view illustrating functional switch of AhpF according to the present invention depending on formation structures of high and low molecular weight complex.

FIGS. 8A and 8B are a graph (FIG. 8A) illustrating a result obtained by expressing a recombinant protein of AhpF of *Pseudomonas aeruginosa* and purifying AhpF using size exclusion chromatography in order to analyze a structure of AhpF according to the present invention and a result (FIG. 8B) obtained by confirming a fraction of each peak of fast protein liquid chromatography (FPLC) using native-polyacrylamide gel electrophoresis (PAGE).

FIGS. 9A and 9B illustrate results of a peroxidase activity (FIG. 9A) and a holdase activity of the chaperone (FIG. 9B) depending on structures of a high molecular weight (HMW) complex and a low molecular weight (LMW) complex of AhpF.

FIGS. 10A, 10B, and 10C, which illustrate a purification result of an AhpF protein using size exclusion chromatography when heat shock is applied to the AhpF protein, illustrate that there was a structural change in AhpF resulting from heat shock.

FIG. 11 illustrates a structure of AhpF according to the present invention and a produced mutant. In FIG. 11, AhpF (PA) indicates AhpF of *Pseudomonas aeruginosa* according to the present invention, AhpF(PP) indicates AhpF of *Pseudomonas putida*.

FIG. 12 is a graph illustrating that in a mutant of AhpF according to the present invention in which cysteine at the position 342 was mutated, a TR activity was increased 2 times or more as compared to wild type AhpF.

FIGS. 13A, 13B, and 13C are photographs illustrating states of $T_3$ generation *Arabidopsis thaliana* transformed by a vector including an AhpF gene and wild-type *Arabidopsis thaliana* after 7 days from heat treatment at a high temperature (42° C.) for 2 hours, which illustrates that *Arabidopsis thaliana* overexpressing the AhpF protein according to the present invention had resistance to heat.

FIGS. 14A, 14B, 14C, and 14D are photographs illustrating whether or not the transgenic *Arabidopsis thaliana* overexpressing the AhpF had thermotolerance after heat stress at 37° C. for 4 days to wild-type *Arabidopsis thaliana* and transgenic *Arabidopsis thaliana* overexpressing the AhpF according to the present invention.

BEST MODE

Hereinafter, the present invention will be described in detail through Examples. The present invention may be modified in various different forms, and is not limited to limited to Examples described below.

<Example 1> AhpF Gene Cloning of *Pseudomonas aeruginosa*

A PaAhpF gene was cloned from genome DNA of *Pseudomonas aeruginosa* PAO1 into a pGEM T-easy vector corresponding to a cloning vector using polymerase chain reaction (PCR), and the gene was confirmed using sequencing analysis. PCR was performed under the following conditions for cloning the PaAhpF gene. A reaction of a mixture of genome DNA (10 ng), dNTP (0.2 µM), a forward primer (20 pmol), a reverse primer (20 pmol), Taq polymerase (1 unit), and distilled water (20 µl) was performed under the conditions: one cycle of pre-denaturation (94° C., 1 minute), 35 cycles of denaturation (94° C., 30 second), annealing (50° C., 45 second), extension (72° C., 45 second), and one cycle of extension (72° C., 10 minutes). In this case, the forward primer was PaAhpF-F(NdeI) 5'-AAGCT CATATGTTGGACGCCAATC-3' (SEQ ID No: 2), and the reverse primer was PaAhpF-R(BamH1) 5'-G GGATCCTCACTCCGGCGCG-3'(SEQ ID No: 3).

<Example 2> Separation and Purification of AhpF Protein of *Pseudomonas aeruginosa*

In order to separate and purify the AhpF protein, the PaAhpF gene cloned into the pGEM T-easy vector in <Example 1> was sub-cloned into pET28a vector using a restriction enzyme site. Sub-cloning of pET28a::PaAhpF was confirmed through sequencing analysis. The PaAhpF protein was over-expressed in *E. coli* (BL21 (DE3)) by adding 0.2 mM IPTG using a T7 promoter system in the pET28a vector. The over-expressed PaAhpF protein to which six histidines were tagged was separated and purified using a Ni-NTA chelate resin.

A purification process of the protein was performed as follows: A 1/100 dilution of a seed culture (pET28a:: PaAhpF in BL21(DE3)) was inoculate into a 2 L Erlenmeyer flask containing 500 mL of LB, and then cultured at 30° C. and 120 rpm. After culturing the diluted seed culture until an $OD_{600}$ reached 0.5, finally, 0.2 mM IPTG was added thereto, and expression of the PaAhpF protein was induced at 30° C. and 120 rpm for 4 hours. Cells were obtained by centrifugation (6000 rpm, 10 minutes, 4° C.) and lysed using a PBS buffer (137 mM NaCl, 27 mM KCl, 10 mM $Na_2HPO_4$, 2 mM $KH_2PO_4$). The cells were lysed using a sonicator, and the cell lysate was subjected to centrifugation (15000 rpm, 40 minutes, 4° C.), thereby separating only a supernatant. The over-expressed paAhpF protein to which histidine was tagged was bound to a resin by adding the cell lysate to a NTA-chelate resin previously equilibrated by affinity chromatography, and then treated with thrombin, thereby separating and purifying the PaAhpF protein. The separated and purified protein was moved to a membrane tube, and then subjected to repetitive dialysis three times in 1 L of 50 mM HEPES (pH8.0) buffer, followed by cryopreservation. Enzyme activities were analyzed using the protein separated and purified as described above.

<Example 3> Analysis of Enzymatic Function of AhpF Protein According to the Present Invention <3-1> Measurement of Peroxidase Activity In order to measure a peroxidase activity, an Ahp reductase system was used. Scavenging of hydrogen peroxide ($H_2O_2$) was indirectly measured by measuring a degree of oxidation of NADH to $NAD^+$ through a change in absorbance at 340 nm. A change in absorbance of a total of 500 µl of a reaction solution (0.3 mM NADH, PaAhpF (1~4 µM), PaAhpC (1~4 µM), 1 mM $H_2O_2$) was measured at 340 nm for 10 minutes.

<3-2> Measurement of Thioredoxin Reductase (TR) Activity

In order to measure a thioredoxin reductase (TR) activity, reduction of Di-thio-bisnitrobenzoic acid (DTNB) was used. In detail, at the time of measuring thioredoxin reductase (TR) activity, first, a reduction rate of DTNB to two molecules of 2-nitro thiobenzoate (TNB) anion was measured at OD 412 nm in an AhpF-free state as a control. A change in absorbance of a total of 500 µl of a reaction solution (50 mM potassium phosphate buffer (pH 8.0), 2 mM EDTA, 5 mM DTNB, 0.3 mM NADH, AhpF (0.1~1 μM)) was measured at 412 nm for 5 minutes. Yeast thioredoxin reductase (yTR) was used as a positive control.

<3-3> Measurement of Thioredoxin (Trx) Activity

In order to measure a thioredoxin (Trx) activity, insulin reductase was used. In general, insulin exists in a state in which α and β chains are linked to each other by disulfide bonds, but in a case in which thioredoxin (Trx) reduces the disulfide bond, the β chain is denatured, thereby forming an aggregate. A degree of formation of the aggregate as described above was determined by measuring absorbance at 650 nm. A change in absorbance of a total of 500 μl of a reaction solution (100 mM potassium phosphate buffer (pH 7.5), mM EDTA, 500 μg insulin, 2 mM DTT, PaPrx (1~10 μM)) was measured at 650 nm for 30 minutes.

<3-4> Measurement of Molecular Chaperone

In general, a molecular chaperone activity is divided into a holdase activity and a foldase activity. In the present experiment, both of the holdase activity and the foldase activity were analyzed. First, the principle for analyzing the holdase activity was as follows: when malate dehydrogenase (MDH), which is sensitive to heat stress, is heated to 43° C., malate dehydrogenase (MDH) is denatured to thereby be aggregated, such that absorbance is increased. However, in a state in which malate dehydrogenase (MDH) coexists with a protein having a molecular chaperone activity, denaturation of MDH is prevented, and thus formation of aggregates is suppressed, such that absorbance is not increased. In the present invention, a change in absorbance of a total reaction solution (50 mM Hepes buffer (pH 7.5), 52 μg MDH, various concentrations of PaAhpF) was measured at 340 nm for 15 minutes using the principle as described above.

In order to measure the foldase activity, after glucose-6-phosphate dehydrogenase (G6PDH) protein was treated with guanidine-HCl to thereby be denatured, a recovered G6PDH activity was measured. A degree of refolding of the total reaction solution was measured. In detail, after 40 μM G6PDH was chemically denatured in a denaturation buffer (50 mM Tris-HCl (pH 7.5), 4 M guanidine-HCl) at room temperature for 2 hours 30 minutes, the denatured G6PDH was diluted 50 times and reacted for 6 hours, 12 hours, and 24 hours in a renaturation buffer (50 mM Tris-HCl (pH 7.5), at various concentrations of AhpF protein or GroEL protein, 10 mM ATP, 10 mM KCl, 2.5 mM MgCl$_2$). Thereafter, an activity of the renatured G6PDH was measured. In detail, NADPH formed in a total of 500 μl of a reaction solution (50 mM Tris-HCl (pH 7.5), 1 mM NADP, 2 mM glucose-6-phosphate (Glucose-6-P), 4 nM renatured G6PDH) was calculated by measuring absorbance at 340 nm for 5 minutes. GroEL was used as a positive control.

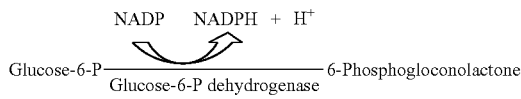

As a result of analyzing the enzymatic activities of AhpF, it may be confirmed that AhpF of *Pseudomonas aeruginosa* had all of the thioredoxin reductase, thioredoxin, peroxidase, and chaperone activities, as illustrated in FIGS. 2, 3A, 3B, 4A, 4B, 5A, and 5B.

<Example 4> Structural Change of AhpF Protein According to the Present Invention and Analysis of Activity Depending Thereon In order to analyze a structure of the AhpF protein, size exclusion chromatography (SEC) was performed. In detail, the AhpF protein and 10 mM Tris-HCl (pH 8.0) buffer solution were passed through a Superdex 200 10/300 GL column at a constant rate (0.5 ml/min) using FPLC (Amersham Biosciences; AKTA). 0.5 ml of the buffer solution and 0.5 ml of the AhpF protein passed through the column were collected at each time. In addition, the collected AhpF protein was largely divided and fractionated into three groups (F1, F2, and F3) depending on protein peaks detected at OD 280 nm. Each of the fractionated proteins was concentrated in order to verify activities of the protein.

<Example 5> Production of Mutant of AhpF Protein and Analysis of Activity Thereof Mutants of a TR domain (AhpF_C), and a Trx domain (AhpF_N) of the AhpF protein and various mutants (C128S, C131S, C342S, C344S, C347S, C342A, C128/131S, C342/344/347S, All C to S_AhpF) in which an active cysteine residue was substituted with serine were produced as illustrated in FIGS. 6 and 11. Each of the proteins from these mutants was separated and purified using affinity chromatography as in <Example 2> and an activity of each of the enzymes was measured by the same method as in <Example 3>.

As a result, the TR activity was decreased in other mutants as compared to a wild type AhpF protein, but in C342S and C342A mutants, the TR activity was increased by two times or more as compared to the wild type AhpF protein (see FIG. 12).

<Example 6> Production of *Arabidopsis thaliana* Transformed by Recombinant Vector into which AhpF Gene is Introduced and Confirmation of Resistance to Heat Shock In order to produce transgenic *Arabidopsis thaliana* overexpressing PaAhpF, a PaAhpF gene was constructed into a pCAMBIA1302 vector corresponding to a transformation vector, and this construct (pCAMBIA1302:PaAhpF) was transformed into *Agrobacterium*. Thereafter, *Arabidopsis thaliana* was transformed. In order to confirm a transformant, a transformant having resistance was selected in hygromycin selective media, and a third-generation (T$_3$) transformant was secured through repetitive selection. Further, PaAhpF protein over-expressed was confirmed in the T$_3$ transformant through a western blotting test.

Thermotolerance of the selected transgenic *Arabidopsis thaliana* overexpressing PaAhpF was verified in a LB media and soil. A test of thermotolerance in the LB media, after *Arabidopsis thaliana* cultivated for 10 days was subjected to heat shock at 42° C. for 2 hours, recovery of *Arabidopsis thaliana* was observed at 22° C. for 3 to 7 days again. A test of thermotolerance in the soil, after *Arabidopsis thaliana* cultivated at 22° C. for 3 weeks was subjected to heat shock at 37° C. for 4 days, recovery of *Arabidopsis thaliana* was observed at 22° C. for 5 days again. The transgenic *Arabidopsis thaliana* overexpressing PaAhpF had resistance to heat in the soil as well as in the LB media (see FIGS. 13A, 13B, and 13C, and FIGS. 14A to 14D).

Although Examples of the present invention have been illustrated and disclosed, those skilled in the art will appreciate that various modifications are possible, without departing from the scope and spirit of the invention, and the scope of the invention will be disclosed by the accompanying claims.

The invention claimed is:

1. A mutant AhpF protein of *Pseudomonas aeruginosa* in which cysteine residue at the position 342 in the amino acid sequence of SEQ ID NO: 1 is substituted with serine.

2. The mutant AhpF protein of claim 1, which is in a complex form, said complex having a molecular weight of 500 to 2000 kDa.

3. The mutant AhpF protein of claim 1, which is in a complex form, said complex having a molecular weight of 100 to 250 kDa.

4. A composition for improving resistance of a plant to oxidative stress or heat stress, the composition comprising a vector containing a polynucleotide encoding the mutant AhpF protein of claim 1.

5. An *Agrobacterium* transformed by a recombinant vector comprising a polynucleotide encoding the mutant AhpF protein of claim 1.

* * * * *

SEQUENCE LISTING

<160> NUMBER OF SEQ ID NOS: 3

<210> SEQ ID NO 1
<211> LENGTH: 521
<212> TYPE: PRT
<213> ORGANISM: Pseudomonas aeruginosa

<400> SEQUENCE: 1

```
Met Leu Asp Ala Asn Leu Lys Thr Gln Leu Lys Ala Tyr Leu Glu Lys
1               5                   10                  15

Val Ser Gln Pro Phe Glu Ile Val Ala Ser Leu Asp Asp Ser Asp Lys
            20                  25                  30

Ser Arg Glu Leu Leu Gly Leu Leu Gln Asp Ile Val Gly Leu Thr Asp
        35                  40                  45

Lys Ile Thr Leu Lys Thr Asp Gly Ser Asp Ala Arg Lys Pro Ser Phe
    50                  55                  60

Ser Leu Asn Arg Pro Gly Ala Asp Ile Gly Leu Arg Phe Ala Gly Ile
65                  70                  75                  80

Pro Met Gly His Glu Phe Thr Ser Leu Val Leu Ala Leu Leu Gln Val
                85                  90                  95

Gly Gly His Pro Ser Lys Leu Asp Ala Asp Val Ile Glu Gln Val Lys
            100                 105                 110

Gly Ile Glu Gly Thr Phe Glu Phe Glu Thr Tyr Phe Ser Leu Ser Cys
        115                 120                 125

Gln Asn Cys Pro Asp Val Val Gln Ala Leu Asn Leu Met Ala Val Leu
    130                 135                 140

Asn Pro Asn Ile Arg His Val Ala Ile Asp Gly Ala Leu Phe Gln Asp
145                 150                 155                 160

Glu Val Glu Ala Arg Gln Ile Met Ser Val Pro Ser Ile Tyr Leu Asn
                165                 170                 175

Gly Glu Val Phe Gly Gln Gly Arg Met Gly Val Glu Glu Ile Leu Ala
            180                 185                 190

Lys Ile Asp Thr Gly Ala Ala Ala Arg Asp Ala Glu Lys Leu Thr Ala
        195                 200                 205

Arg Asp Ala Phe Asp Val Leu Val Val Gly Gly Pro Ala Gly Ala
    210                 215                 220

Ala Ala Ala Ile Tyr Ala Ala Arg Lys Gly Ile Arg Thr Gly Val Ala
225                 230                 235                 240

Ala Glu Arg Phe Gly Gly Gln Val Leu Asp Thr Met Ala Ile Glu Asn
                245                 250                 255

Phe Ile Ser Val Gln Glu Thr Glu Gly Pro Lys Leu Ala Arg Ala Leu
            260                 265                 270

Glu Glu His Val Arg His Tyr Glu Val Asp Ile Met Asn Leu Gln Arg
        275                 280                 285

Ala Ser Lys Leu Val Pro Ala Lys Asn Ala Gly Glu Leu His Glu Val
    290                 295                 300

Arg Phe Glu Ser Gly Gly Ser Leu Lys Ala Lys Thr Leu Ile Leu Ala
305                 310                 315                 320

Thr Gly Ala Arg Trp Arg Glu Met Gly Val Pro Gly Glu Gln Glu Tyr
                325                 330                 335

Lys Ala Lys Gly Val Cys Phe Cys Pro His Cys Asp Gly Pro Leu Phe
            340                 345                 350

Lys Gly Lys Arg Val Ala Val Ile Gly Gly Asn Ser Gly Val Glu
        355                 360                 365
```

```
Ala Ala Ile Asp Leu Ala Gly Ile Val Ala His Val Thr Leu Leu Glu
        370             375             380

Phe Asp Ser Lys Leu Arg Ala Asp Ala Val Leu Gln Arg Lys Leu Tyr
385             390             395                 400

Ser Leu Pro Asn Val Glu Val Ile Thr Ser Ala Leu Thr Ser Glu Val
            405             410                 415

Lys Gly Asp Gly Gln Lys Val Thr Gly Leu Val Tyr Lys Asp Arg Asn
            420             425             430

Ser Glu Glu Phe Lys Ser Ile Glu Leu Glu Gly Ile Phe Val Gln Ile
        435             440             445

Gly Leu Leu Pro Asn Thr Glu Trp Leu Lys Gly Ser Val Glu Leu Ser
    450             455             460

Pro Arg Gly Glu Ile Ile Val Asp Ala Arg Gly Glu Thr Ser Leu Pro
465             470             475                 480

Gly Ile Phe Ala Ala Gly Asp Val Thr Thr Val Pro Tyr Lys Gln Ile
                485             490             495

Val Ile Ala Val Gly Glu Gly Ala Lys Ala Ser Leu Ser Ala Phe Asp
            500             505             510

His Leu Ile Arg Thr Ser Ala Pro Glu
        515             520

<210> SEQ ID NO 2
<211> LENGTH: 24
<212> TYPE: DNA
<213> ORGANISM: Artificial Sequence
<220> FEATURE:
<223> OTHER INFORMATION: PaAhpF forward primer

<400> SEQUENCE: 2
aagctcatat gttggacgcc aatc                                          24

<210> SEQ ID NO 3
<211> LENGTH: 20
<212> TYPE: DNA
<213> ORGANISM: Artificial Sequence
<220> FEATURE:
<223> OTHER INFORMATION: PaAhpF reverse primer

<400> SEQUENCE: 3
gggatcctca ctccggcgcg                                               20
```